United States Patent
Ott

[11] 4,089,054
[45] May 9, 1978

[54] DEVICE FOR MEASURING THE THICKNESS OF LAYERS WITH A RADIONUCLIDE IRRADIATING THE LAYER

[76] Inventor: Albert Ott, Sindelfinger Strasse 118, 7032 Sindelfingen 6, Germany

[21] Appl. No.: 691,039

[22] Filed: May 28, 1976

[30] Foreign Application Priority Data

Mar. 18, 1976 Germany .............................. 2611411

[51] Int. Cl.² ...................... G06F 15/20; G01N 23/20
[52] U.S. Cl. .................................... 364/527; 250/272; 250/308; 364/563; 364/571
[58] Field of Search ........................... 235/151.3, 197; 250/272, 308, 358 R, 336, 341

[56] References Cited

U.S. PATENT DOCUMENTS

| | | | |
|---|---|---|---|
| 3,405,267 | 10/1968 | Chope | 250/308 |
| 3,588,507 | 6/1971 | Weinstock | 250/308 |
| 3,639,763 | 2/1972 | Streng | 250/308 |
| 3,665,199 | 5/1972 | Cahill et al. | 250/308 |
| 3,854,042 | 12/1974 | Ott | 250/272 |
| 4,009,376 | 2/1977 | Faraguet | 235/151.3 |

*Primary Examiner*—Malcolm A. Morrison
*Assistant Examiner*—Errol A. Krass

[57] ABSTRACT

A normalized count from a digital computer in a layer-thickness measuring device of the beta ray back-scatter type, is fed to a digital-analog converter and a correction circuit which realizes the function $X_{n\ corr} = X_n + A\ a_2 X_n^p (1-x_n)^q$ and then to an indicator having a non-linear scale, in which $X_n$ is the normalized count, $A$ is a dimensionless number between $+1$ and $-1$, $a_2$ is a dimensionless number between $n+0.1$ and $-0.1$, and $p$ and $q$ are dimensionless positive values around unity but different from one another which are permanently wired into the correction circuit.

5 Claims, 7 Drawing Figures

DEVICE FOR MEASURING THE THICKNESS OF LAYERS WITH A RADIONUCLIDE IRRADIATING THE LAYER

The present invention relates to a device for measuring the thickness of layers by the Beta-ray back-scatter method, with a radionuclide irradiating the layer which radionuclide produces radiation whose energy corresponds to the thickness of the layer, with a detector which receives the back-scatter radiation, which comes from the layer and a possible carrier material, as count X and produces at its output a pulse rate, in the region between a lower first count $X_0$ corresponding to the back-scatter associated with zero layer thickness, and an upper count $X_S$ associated with the range of an infinitely thick layer, and with a digital computer which computes the standard count $$X_n = \frac{X - X_O}{X_S - X_O}$$

Through U.S. Pat. No. 3,854,042 it is known how to form the magnitude $X_n$ in a computer in the course of processing the pulses coming from the counter tube. This has the advantage that the display data no longer have to be taken into consideration. Depending on the measurement problem (different carrier materials, different layer materials), radiator used, diaphragm opening, diaphragm distance, etc., the number of output impulses moves between widely differing orders of magnitude. However, if the standardized count $X_n$ is formed in an installed computer, the output magnitudes are between zero and plus one, where $X_0$ is the back-scatter rate for uncoated carrier material and where $X_S$ is the back-scatter rate from a quasi infinitely thick layer of the material present on the carrier layer.

One may consider the nonlinear relation between the count rate (be it standardized or not) and the layer thickness by an equalizing function, as stated in U.S. Pat. No. 3,854,042. One may also allow for this nonlinear relation with analog displays by using scales with nonlinear scale graduations. In either case, one starts with a calibration curve as shown in FIG. 2 of the aforementioned patent document.

In reality, however, the totality of actually existing calibration curves is not along a single line, but in a band on both sides of the mean calibration curves, with this mean calibration curve located in the center of the band. These deviations on both sides of the calibration curves may be of the order of 10%. These deviations are misleading, because the Beta back-scatter method is based on statistical laws, i.e., a certain layer thickness is only statistically and not absolutely associated with a certain scatter rate. If errors occur in the test result, doubts arise whether the deviations are statistical ones or whether they are due to the deviation of the actual curve from the calibration curve. In addition, errors of the order of ± 10% maximum can no longer be considered as small.

The deviation of the actual curve from the calibration curve may be caused as follows: During the preparation of the calibration curve, a dimming ring different from the one used during the test may have been used. This applies both to the form of the dimming ring opening and to the area of the dimming ring opening. The distance of the front surface of the radionuclide from the test object may have been different during the preparation of the calibration curve than during the actual test. The Beta ray bundle, emitted by the radionuclide, may have been collimated differently during the calibration than during the actual test. An aggravating case which frequently occurs in practice is the following: During preparation of the calibration curve, a certain uncoated carrier material has been used (e.g., nickel). However, as a rule the alloy of the carrier material during preparation of the calibration curve is different from the alloy used during the actual test (e.g., a different nickel alloy).

It is, therefore, an object of the present invention to provide a device of the initially described type by means of which the aforementioned errors can be virtually reduced to zero and operation can be handled, nevertheless, by untrained personnel.

The objects of the present invention are achieved by the improvements as follows:

The device comprises a radionuclide irradiating the layer, which radionuclide produces radiation whose energy corresponds to the thickness of the layer, each radionuclide/layer material/and if present, carrier material - combination defining a special test problem, a detector which receives the backscatter radiation, which comes from the layer and a possibly present carrier material and produces at its output a pulse count, X, in the region between a lower first count $_0$ corresponding to the backscatter associated with zero layer thickness, and an upper count $X_S$ associated with the range of an infinitely thick layer, and a digital computing means connected to said detector. The digital computing means comprises means for dividing the difference between the detected pulse count, X, and the lower first count, $X_0$, by the difference between the upper pulse count, $X_S$ and the lower first pulse count $X_0$, to calculate from the output pulse count from the detector a normalized pulse count $$X_n = \frac{X - X_O}{X_s - X_O},$$

The digital computing means is connected to a digital-analog converter and the digital to analog converter is connected to an analog correction circuit. The correction circuit realizes a function $X_{n\ corr} = X_n + A [a_2 X_n^p (1-x_n)^q]$ and generates an output signal in proportion to this function. An indicator instrument receives the analog signal from the correction circuit corresponding to $X_n$ corr and has an interchangeable, non-linear scale calibrated in thicknesses with respect to the special test problem. And means for externally setting the magnitude A of the correction function are provided; where $A$ is a dimensionless number between +1 and −1, $a_2$ is a dimensionless number between +0.1 and −0.1, $p$ and $q$ are dimensionless positive values, between 0.5 and 1.5 but different from one another, and which are realized by a permanently wired equipment of the correction circuit.

By means of $a_2$ being within ±0.05, one obtains a simpler corrective circuit which is sufficient for all practical cases.

$p$ and $q$ being between 0.7 and 1.3 permit a simplification of the function generator producing the function.

By means of the improvements as follows, one can, in addition, correct parallel displacements. The correction circuit realizes $X_{n\ corr} = X_n + A [a_0 + a_2 x_n^p (1-x_n)^q]$ where $a_0$ is a dimensionless number within ± 0.1 which states the horizontal parallel displacement of the function $X \; X_{n \, corr}$ from $X_n$.

By means of the following improvements, changes in slope can also be corrected. The correction circuit realizes $X_{n \, corr} = X_n + A \, [a_0 + a_1 X_n + a_2 X_n^p (1 - X_n)^q]$ where $a_1$ is a dimensionless number within $\pm \, 0.1$ which indicates the slope of function $X_{n \, corr}$ of $X_n$.

The invention is being explained on an embodiment in accordance with the present invention.

Figure 1:
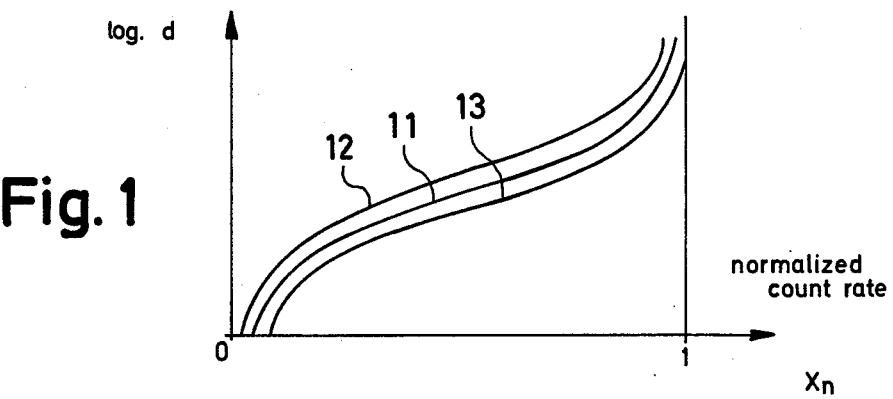
FIG. 1 shows a logarithmic plot of the thickness of a layer to be measured in relation to the normalized pulse count $X_n$.

In FIG. 1, the vertical coordinate represents the logarithm of the layer thickness, and the horizontal coordinate represents the standardized count rate $X_n$. The values for $X_n$ may be between zero and one (unity). Curve 11 is the calibration curve which is ordinarily obtained by the manufacturer of the devices and on which the scale applying to the test task is realized. Logarithmic scale is chosen because in the middle region, which is of most interest to the test, there is a nearly linear relation between the layer thickness d and the standardized count rate $X_n$. Curves 12 and 13 define the outer limits of a band around curve 11. The curves actually occurring during the test are located inside this band. In practice, the deviations of the upper and lower curves 12, 13 at $X_n = 0.5$ are about $\pm \, 10\%$. The formula in accordance with the present invention, or the circuit realizing it, operates precisely as required in the present case, which is easily evident for the end points from the considerations: If in $X_{n \, corr} = X_n + A[a_2 X_n^p (1 - X_n)^q]$ the value $X_n = 0$, the correction also becomes 0. This means, that in the left bottom area, where the curves anyhow tend to zero, nothing is corrected.

However, if $X_n = 1$, the correction also becomes 0. This also is correct because for $X_n = 1$ the curves 11, 12, 13 meet at the same point which for practical purposes is assumed to be infinity.

In between, the function $X_n$ corr has its maximum value. Assuming as correction in the middle (i.e. for $X_n = 0.5$) a correction of $\pm 10\%$, the values A and $a_2$ can be easily computed. If necessary, this can be done by two to three iterations. Of course, the values of A and $a_2$ are different when assuming $a \pm 5\%$ correction.

p and q are dimensionless magnitudes which indicate the characteristic behavior of the curve 24 (to be discussed later), i.e., whether this curve is flat or steep and where its maximum lies. Values p and q may be the same or unequal. In the majority of cases they are unequal and have values from approximately 0.7 to 1.3. Normally p is smaller than 1 when q is larger than 1. The same applies vice versa.

The individual values, stated in the claims and reproduced by electrical circuits, are obtained as follows:

1. One obtains for all technically important dimming ring shapes and dimensions $d = f(X_n)$, i.e., for all important combinations of coating material and base material. A family of so-called calibration curves is obtained for each test task.

2. If, within a test assignment, one has measured k types of dimming rings in this manner, one can state a mean characteristic curve which is defined by forming for each given $X_n$ the mean value of the associated layer thicknesses $d_i (i = 1 \ldots k)$ $$d_m = \frac{1}{k} \sum_{i=1}^{k} d_i \quad (X_n \text{ is the same for all } d_i \text{ within a sum!})$$

This procedure is carried out for suitably selected $X_n$ values between $0 \leq X_n \leq 1$. The result defines the middle characteristic curve of the test assignment $$d_m = f_m(X_n)$$

this middle characteristic curve is realized in the scale (to be discussed later) of the instrument; such a scale applies for a certain test assignment, i.e. for a definite combination of layer material and carrier material.

3. Now one considers the fine structure of the measurement taks, i.e., one seeks a solution of the problem of bringing about the correct instrument indication for any dimming ring. The indication applying to each individual dimming ring can be obtained only by correcting the $X_n$ value found by test, hence the magnitude $$X_{n \, corr} = g(X_n)$$

The question is what function to use for this correction. For the points $X_n = 0$ and $X_n = 1$ this question can be answered at once: A correction for $X_n$ must not take place at these points since the reference points for the standardization by definition are independent of the particular dimming ring. For the $X_n$ values between 0 and 1, one proceeds as follows: One takes a layer each in the lower, middle and upper characteristic curve region and determines $X_n$ by measurement and $X_{n \, corr}$ from the middle characteristic realized on the scale. Hence $X_{n \, corr}$ is that value which would have to be present to produce the correct layer indication on the realized scale. One forms now the difference $X_n - X_{n \, corr}$ and plots this difference as ordinate against the value $X_{n \, corr}$ as abscissa. One finds that the mentioned 5 points ($d = 0, d = \infty$, layer in the lower, middle and upper characteristic curve region) define a curve represented by line 15 in FIG. 2. Continuing this procedure for all dimming rings, one finds to one's surprise that the five-point curves are geometrically similar to each other for all dimming rings so that they can be derived from a single master curve by multiplying by a factor A. The factor A lies between $-1$ and $+1$. Of course there also exist dimming rings for which the factor A = 0 holds, i.e., the characteristic of this dimming ring coincides with the middle characteristic without correction.

The result obtained is very important for the practical application. Since all five-point curves are similar to each other and are derived from a master curve, they can be carefully realized in the device with great electronic effort, while for the user of the device only one adjustment knob for setting magnitude A is available.

4. The next question deals with the realization of the five-point curve. It was found that the master curve from which the individual points are derived by multiplying with factor A are the same for different dimming rings within the test assignment; one also find that the five-point curves of different test assignments are similar to each other. In accordance with the present invention, it was found that the five-point curve can be very well realized with the function $$\Delta X_n = X_{n\,corr} - X_n = A\,[a_2 X_n^p (1 - X_n)^q]$$

Figure 2:
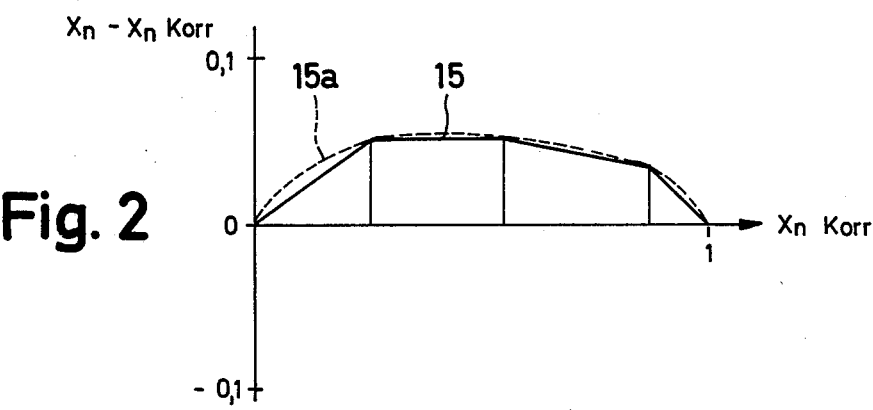
FIG. 2 shows the influence of a correction function $X_n$corr on the normalized pulse count $X_n$ in a plot $X_n - X_n$ corr against $X_n$.

The associated curve is curve 15a in FIG. 2.

5. There are several applications where it is expedient to make a further correction which, deviating from the above, effects a correction at reference points $X_n = 0$ and $X_n = 1$ also. A linear transformation of $X_n$ was found expedient, namely $$a_0 + a_1 X_n$$

which is additively superposed on the correction mentioned in Item 4, so that there finally follows as final total correction function $$X_n = X_{n\,corr} - X_n = A\,[a_0 + a_1 X_n + a_2 X_n^p (1 - X_n)^q]$$

and from there $$X_{n\,corr} = X_n + A\,[a_0 + a_1 X_n + a_2 X_n^p (1 - X_n)^q]$$

Figure 3:
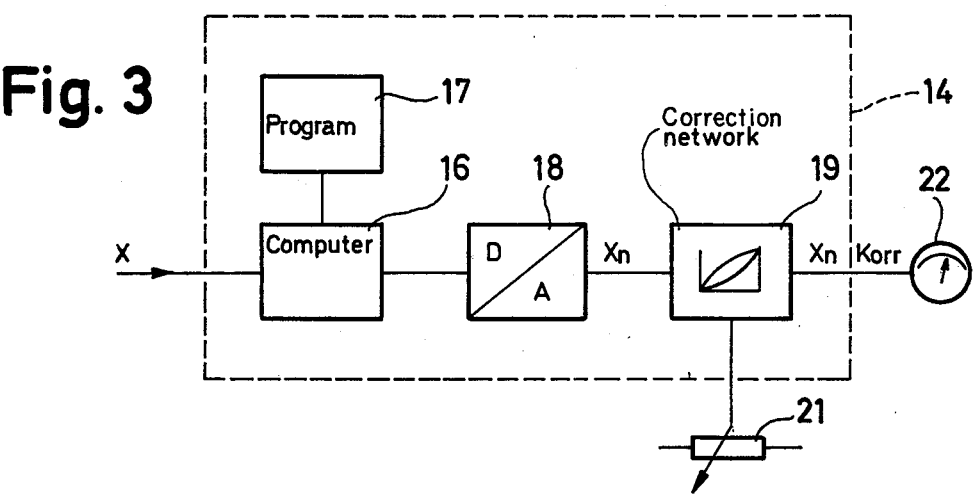
FIG. 3 shows a block diagram of the electronic evaluation circuitry of a device according to the invention comprising an analog correction circuit.

It should be pointed out once more, that the user of the device has access only to the magnitude A and that all other constants and coefficents are fixed values built into the device According to FIG. 3, a device 14 receives from the left-hand side, from a Geiger-Muller counting tube (not shown), the impulses X corresponding to the back-scatter rate. It should be noted that it need not be back-scattered radiation, even though this method is used in 90% of all cases. With very strong rays and/or very thin layers, one may also measure with the same known probes by means of the ray penetration method (transmission method). The impulses X are applied to a digital computer which is controlled by a program transmitter 17. The program transmitter 17 obtains the value for $X_0$ and the value $X_S$ a read-only storage (ROM) and now can compute the standardized count $X_n$ on the basis of the incoming impulses X. This is known and not a subject of the present invention.

However, it is important that up to the computer output, digital processing is used because with these digital computers, the drift always present in analog circuits plays no part. As a result, even when computing small differences the computer makes no errors, e.g., the numerator of the standardization equation may come close to zero. The same holds for the denominator. In addition, the absolute values for $X_0$, $X_S$ and X with one measuring problem may be very large and with anoter may be very small.

The output of computer 16 feeds a digital/analog converter 18 which at its output provides $X_n$ in the form of an analog voltage. This analog voltage $X_n$ is delivered to a correction circuit 19 in which the two limit curves of the correction function are drawn symbolically. The correction circuit 19 can be adjusted from the outside by a knob 21 on device 14. At the output of correction circuit 19, the value $X_{n\,corr}$ appears as analog voltage which value is a measure of the layer thickness d (FIG. 1.). This voltage $X_{n\,corr}$ is applied to an analog display device 22 whose scale (yet to be discussed) is drawn in accordance with calibration curve 11, the middle characteristic curve of the specific measuring assignment.

Figure 4:
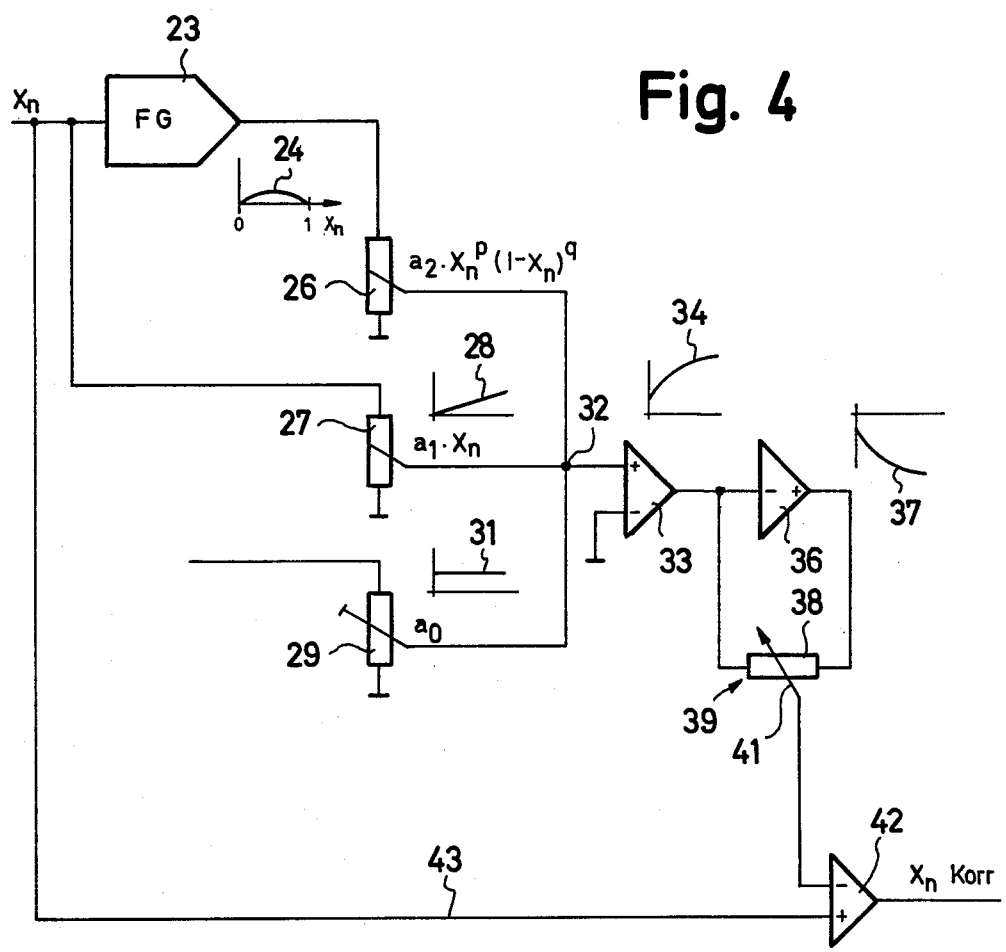
FIG. 4 shows a detailed block diagram of the correction circuit according to FIG. 3.

There are various ways of realizing the correction function electrically by means of packages. One of these is shown in FIG. 4. The analog voltage $X_n$ is delivered to a function generator 23. The latter is a diode circuit and works in analog fashion. When costs play no part, such a function generator, of course, might also be digital. Depending on the size of $X_n$, the function generator 23 realizes the curve 24 which, except for a similarity factor, is identical with line 15a. This signal is applied to a first potentiometer 26 from whose output the function $a_2 X_n^{p(1 - X_n)q}$ can be taken off. Hence the potentiometer furnishes the factor $a_2$.

The value $X_n$ is also applied to a second potentiometer 27 whose output signal runs in accordance with curve 28. This is an ascending straight line. The potentiometer 27 realizes the factor $a_1$. A third potentiometer 29 receives the voltage "1." Depending on the position of the center pickoff of the potentiometer 29, there appears at its output a voltage which is independent of $X_n$. Hence the potentiometer 29 realizes the sum term $a_0$. Hence potentiometer 29 realizes the horizontal straight line 31. The outputs of potentiometers 26, 27, 29 are delivered to point 32 which is the plus input of a summing amplifier 33.

Hence, if all function terms $a_0$, $a_1 X_n$ and $a_2 X_n^{p(1-X_n)q}$ are present, there develops the curve 34 shown near summing amplifier 33. If the center pickoffs of potentiometers 27, 29 were all the way at the bottom, i.e., if $a_0$ and $a_1 = 0$, curve 34 would be identical with curve 24 except for the proportionality factor $a_2$. If only the value $a_0$ were not present, curve 34 would start in the coordinate origin. If $a_1 = 0$, the right-hand terminal point of curve 34 would be just as high as its left-hand terminal point.

The output of summing amplifier 33 is supplied to the minus input of an inverter 36 whose output provides curve 37 which is obtained by a reflection of curve 34 on the horizontal axis. Parallel to the inverter 36 is the resistance 38 of a potentiometer 39 whose pickoff 41 is movable in the conventional manner and is connected to the minus input of a summing amplifier 42 whose plus input via a line 43 receives the same voltage $X_n$ as the function generator 23. At the output of the summing amplifier 42, voltage $X_{n\,corr}$ is obtained.

Figure 5:
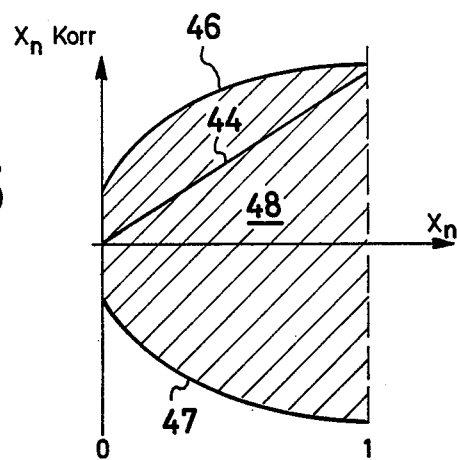
FIG. 5 is a diagrammatic representation of the variation range within which the normalized count rate is adjustable by means of the correction circuit as illustrated in FIG. 4.

The potentiometers 26, 27, 29 and hence the values $a_0$, $a_1 X_n$ and $a_2 X_n^{p(1 - X_n)q}$ are fixed internal settings. For most practical cases it is sufficient to realize only function A $a_2 X_n^{p(1 - X_n)q}$ Conditions are shown graphically in FIG. 5. If the pickoff 41 is in the center, none of curves 34, 37 predominates and $X_n$ and $X_{n\,corr}$ in accordance with straight line 44 are identical throughout the region. If the pickoff 41 is on the extreme left, only curve 34 has an influence. In FIG. 5 it appears as curve 46 with the multiplier component originating with $X_n$ and the additive component. If the pickoff 41 is on the extreme right, only curve 37, which in FIG. 5 together with an additive component yields curve 47, is present. The area between curves 46 and 47 is the shaded correction area 48.

Figure 6:
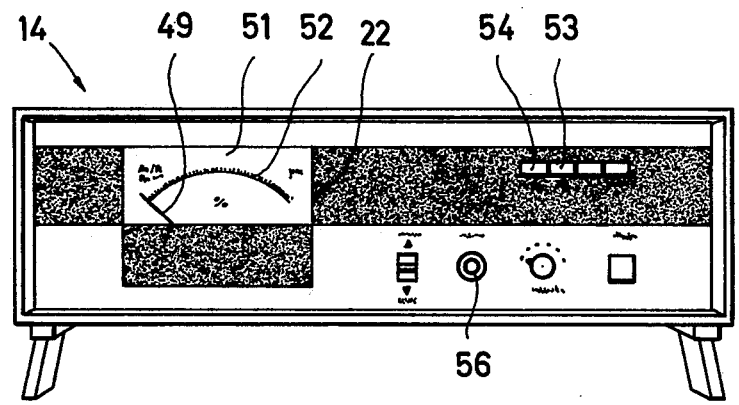
FIG. 6 shows the front view of a device in accordance with the present invention, comprising an analog indication instrument which is adaptable to a great variety of measuring problems.
Figure 7:
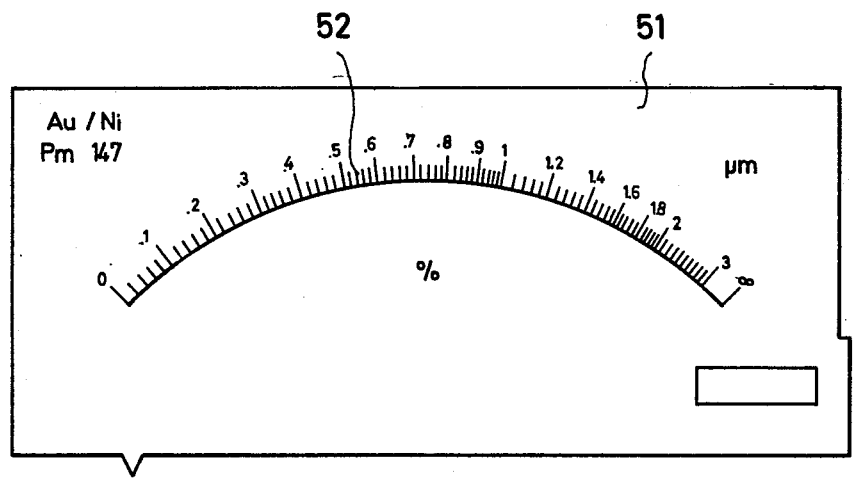
FIG. 7 shows the scale of the analog indication instrument according to FIG. 6.

The device 14, shown accurately in FIG. 6, comprises the indicator 22 which has a pointer 49. Its scale 51 is interchangeable. As shown in FIG. 7, the scale is for the test problem gold on nickel, the radiator is promethium 147 and the usable measuring range is between zero and approx three microns. There is a different scale for any other test problem, e.g., silver on nickel, etc., available from the manufacturer of the device. The graduation spacing on scale 52 corresponds to calibartion curve which was determined by the manufacturer. The measurement with the device proceeds as follows:

The user places a piece of gold with a thickness equal to or larger than the saturation thickness on the probe and presses button 53. The device, through a program control not discussed here, determines the saturation layer thickness $X_S$. Then the user places the uncoated material on the probe and presses button 54. Now device 14 determines $X_0$ in a similar manner. As a result, these values are in the storage section of the program transmitter 17. Now the user places on the probe nickel coated with gold, knowing the thickness of the gold layer, with this thickness being expediently in the mid-portion of the scale graduation 52. In the case shown, the gold might have the thickness of one micron. Depending on the dimming ring, pointer 49 will not come to rest at the 1 micron value, but at the right or left of it. Now the user turns knob 41 which in device 14 is a rotary knob 56. This is done so far and in such a direction that now the pointer 49 is at "1 micron." Now all preliminary work has been done. The user inserts nickel with a gold coating of unknown thickness and this value can new be read. The entire process takes hardly 2 minutes which is very short considering the accuracy achieved. It should be considered that the values for $X_0$, $X_S$ are measured for four times the actual test time. The test time for these magnitudes is 20 seconds each, while the actual test is 5 seconds.

Of course, the known gold layer may also be 0.4 or 0.5 or 0.6 microns, etc.

What is claimed is:

1. A device for measuring the thickness of layers of solid materials, such as of thin metal layers on a carrier layer of another metal, by the Beta ray backscatter method, comprising
   a radionuclide irradiating the layer, which radionuclide produces radiation whose energy corresponds to the thickness of the layer, each radionucilide/layer material and if present, carrier material- combination defining a special test problem.
   a detector which receives the backscatter radiation, which comes from the layer and a possibly present carrier material and produces at its output a pulse count, X, in the region between a lower first count $X_0$ corresponding to the backscatter associated with zero layer thickness, and an upper count $X_s$ associated with the range of an infinitely thick layer, and
   a digital computing means connected to said detector, said digital computing means comprising means for dividing the difference between the detected pulse count, X, and the lower first count, $X_0$, by the difference between the upper pulse count, $X_s$ and the lower first pulse count $X_O$, to calculate from the output pulse count from the detector a normalized pulse count $$X_n = \frac{X - X_O}{X_s - X_O}$$

wherein:
   said digital computing means is connected to a digital to analog converter and said digital to analog converter is connected to an analog correction circuit, having a permanently wired portion, said correction circuit realizing a function $X_{n\ corr} = X_n + A[a_2 X_n^p (1-X_n)^q]$ and generating an output signal in proportion to this function, and wherein an indicator instrument for receiving said analog signal from the correction circuit corresponding to $X_{n\ corr}$ and having an interchangeable, non-linear scale calibrated in thickness with respect to the special test problem, and
means for externally setting the magnitude A of the correction function are provided, where $A$ is a dimensionless number between $+1$ and $-1$, $a_2$ is a dimensionless number between $+0.1$ and $-0.1$, $p$ and $q$ are dimensionless positive values substantially between 0.5 and 1.5 but different from one another, and which are realized by said permanently wired portion of the correction circuit.

2. The device as defined in claim 1 wherein $a_2$ is within $\pm 0.05$.

3. The device as defined in claim 1 wherein $p$ and $q$ lie between 0.7 and 1.3.

4. The device as defined in claim 1 wherein the correction circuit realizes $X_{n\ corr} = X_n + A[a_0 + a_2 X_n^p (1-X_n)^q]$ where $a_0$ is a dimensionless number within $\pm 0.1$ which states the horizontal parallel displacement of the function $X_n$ corr from $X_n$.

5. The device as defined in claim 1 wherein the correction circuit realizes $X_{n\ corr} = X_n + A[a_0 + a_1 X_n + a_2 X_n^p (1-X_n)^q]$ where $a_1$ is a dimensionless number within $\pm 0.1$ which indicates the slope of function $X_{n\ corr}$ of $X_n$.

* * * * *